United States Patent [19]

Napetschnig

[11] 4,245,496

[45] Jan. 20, 1981

[54] PORTABLE MATERIAL HARDNESS TESTER

[76] Inventor: Fred Napetschnig, 120 Mariner Green Ct., Corte Madera, Calif. 94925

[21] Appl. No.: 57,285

[22] Filed: Jul. 13, 1979

[51] Int. Cl.³ .............................................. G01N 3/44
[52] U.S. Cl. ...................................................... 73/83
[58] Field of Search ...................... 73/81, 83; 364/506, 364/508, 550, 556

[56] References Cited

U.S. PATENT DOCUMENTS

| | | | |
|---|---|---|---|
| 2,839,917 | 6/1958 | Webster | 73/81 |
| 3,367,174 | 2/1968 | Afri | 73/83 |
| 4,023,401 | 5/1977 | Ernst | 73/81 |
| 4,116,048 | 9/1978 | Appleford et al. | 73/83 |

Primary Examiner—James J. Gill
Attorney, Agent, or Firm—Warren, Chickering & Grunewald

[57] ABSTRACT

A portable hardness tester including a surface sensing member yieldably mounted for engagement with the surface of material to be tested and a penetrator yieldably mounted adjacent the sensing member for joint contact with the surface; manually applied means for applying minor and major penetrating forces on the penetrator; and electronic means for sensing the differential movement between the penetrator and surface sensing member and translating such differential movement into a hardness indication.

17 Claims, 8 Drawing Figures

PORTABLE MATERIAL HARDNESS TESTER

BACKGROUND OF THE INVENTION

1. Field of Invention

The invention relates to material hardness testers which convert, or afford readings to convert, the displacement of a penetrator into the material being tested into a hardness indication such as a number on a Brinell Scale or the like.

2. Description of Prior Art

Available portable hardness testers may be typically characterized as mechanical devices having penetrators mechanically coupled to dial indicators or the like for furnishing a correlation between a depth of penetration of the penetrator into the material being tested and the hardness of the material, or furnishing displacement readings enabling the user to compute such hardness. Portable hardness testers in common use require careful cleaning and polishing of the surface of the material being tested in order to obtain useful hardness readings, and even with such surface preparation the testers lack accuracy and dependable repeatability, and are subject to malfunctioning due to high or low temperatures and wear of critical parts.

SUMMARY OF THE INVENTION

The portable hardness tester of the present invention uses a penetrator which is driven into the surface of the material being tested for hardness and wherein all measurements are taken from the surface of the material by an organization of a minimum number of closely spaced parts, thus minimizing errors as otherwise introduced in measuring relative penetrator displacement over larger dimensions such as arbors or the like with attendant aberrations introduced by strain and thermal expansion and contraction.

Another feature of the present invention is to provide a portable material hardness tester of the character described which uses electronic sensing very close to the point of penetration thus affording high accuracy and dependable repeatability in use with relatively small, easily applied penetration.

Another object of the present invention is to provide a portable material hardness tester of the character above which will maintain its precision over a wide range of temperature as may be encountered in field use.

A further object of the present invention is to provide a portable material hardness tester of the character described which will work with all materials as found in the field without need for cleaning and polishing the surface prior to testing and without requiring the material to be brought into a shop or laboratory for surface preparation prior to testing.

Still another object of the present invention is to provide a portable material hardness tester of the character above which may be easily and readily manually applied to the work being tested, which will function in essentially a fool-proof manner, and which has the ability to measure the hardness of material having either flat or curved or other non-planar surface.

The invention possesses other objects and features of advantage, some of which of the foregoing will be set forth in the following description of the preferred form of the invention which is illustrated in the drawings accompanying and forming part of this specification. It is to be understood, however, that variations in the showing made by the said drawings and description may be adopted within the scope of the invention as set forth in the claims.

DETAILED DESCRIPTION OF THE INVENTION

Figure 3:
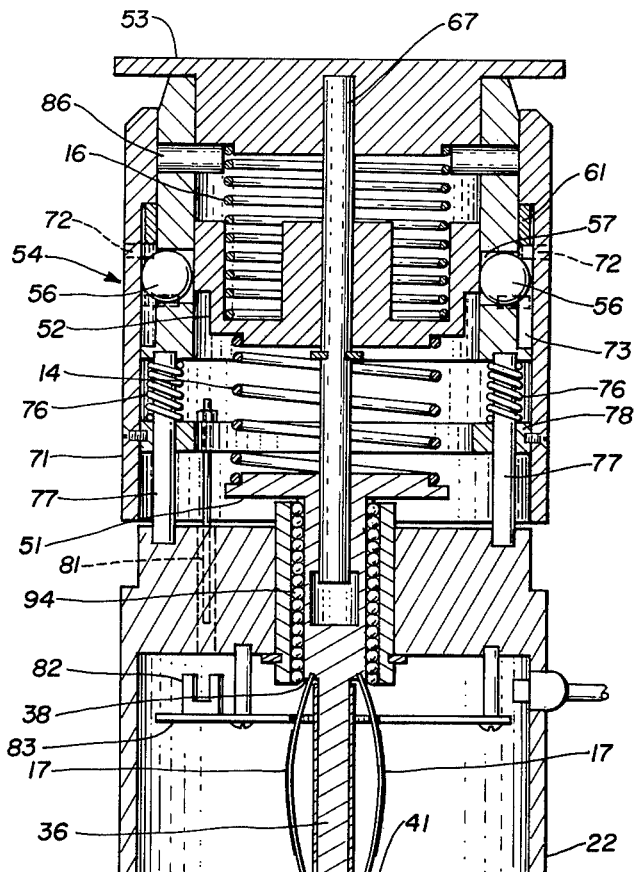
FIG. 3 is a longitudinal sectional view similar to FIG. 1 but showing the parts in a different position.
Figure 4:
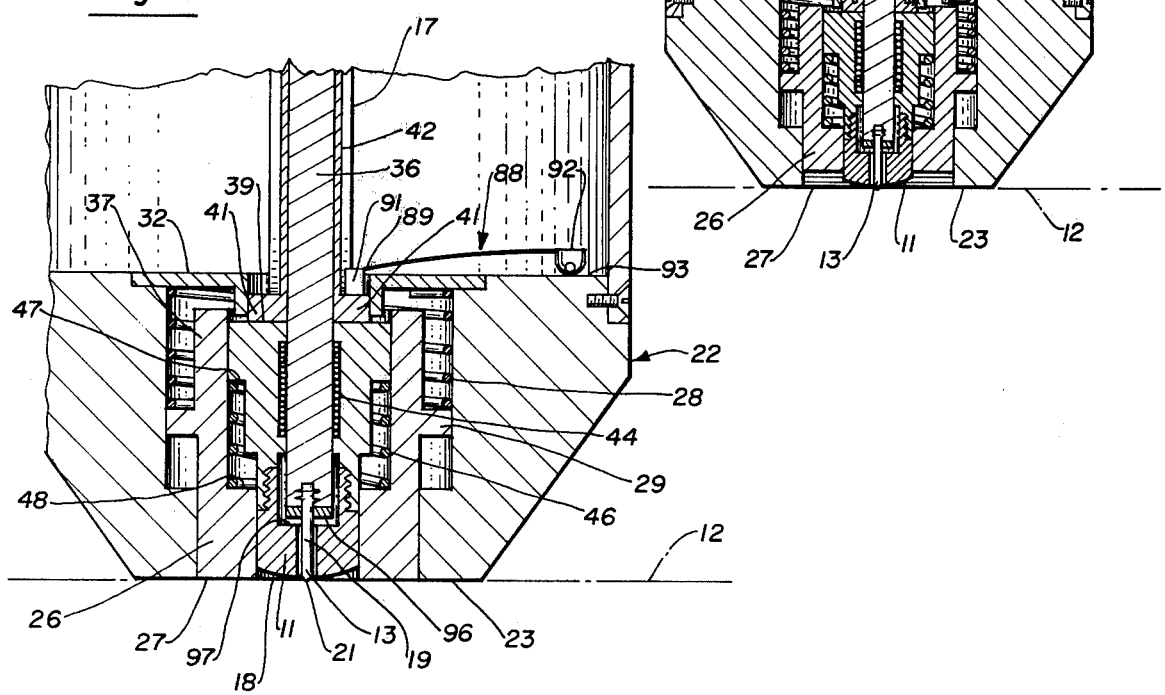
FIG. 4 is a fragmentary cross-sectional view of the tester on an enlarged scale and taken at substantially right angles to the position of view of FIG. 3.
Figure 5:
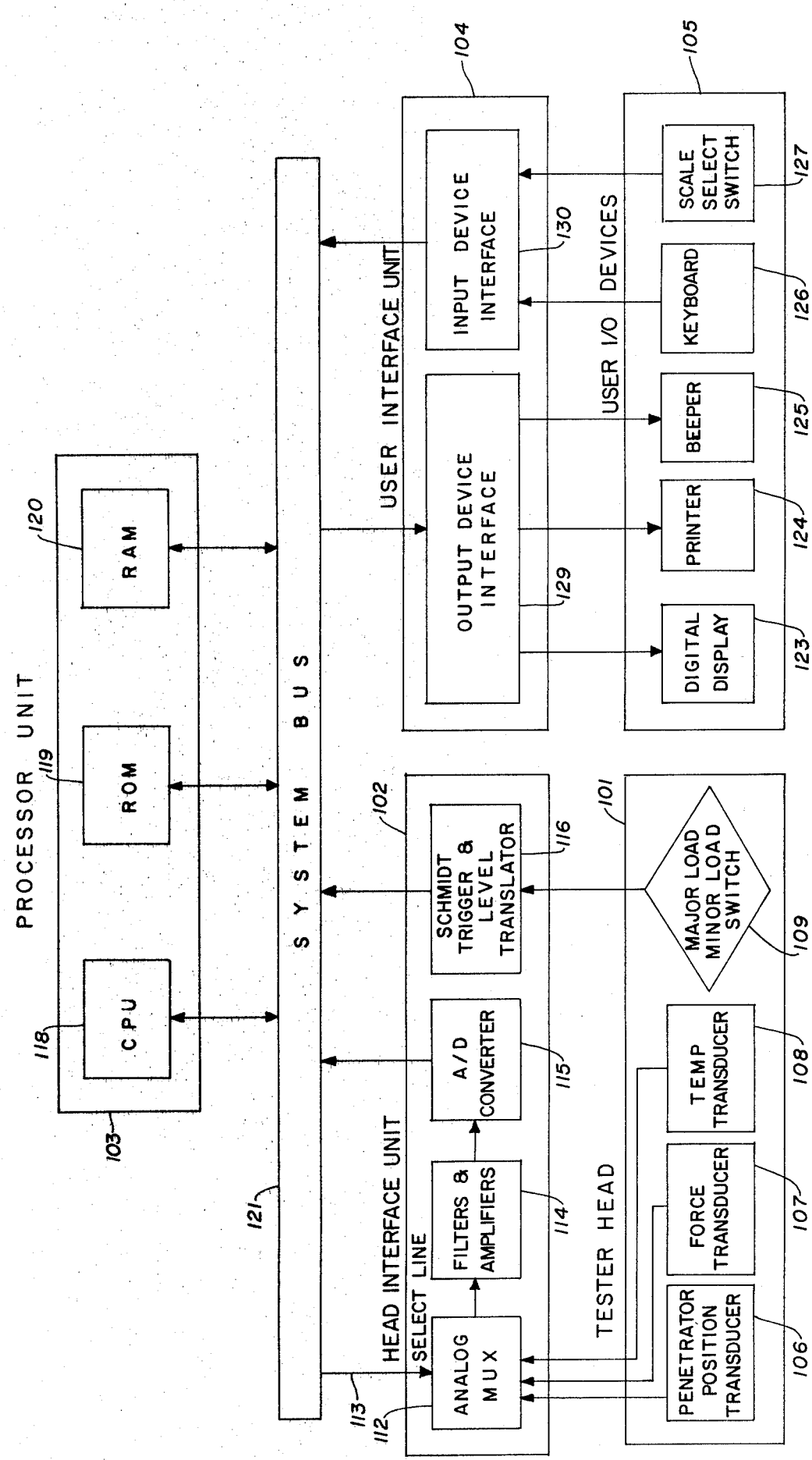
FIG. 5 is a block diagram of the electronic circuitry of the hardness tester of the present invention.

The portable material hardness tester of the present invention comprises briefly a surface sensing member 11 yieldably mounted for engagement with the surface 12 of material to be tested; a penetrator 13 yieldably mounted adjacent member 11 for joint contact with surface 12, see FIGS. 3 and 4; means 14 for placing a first predetermined surface penetrating force on penetrator 13; means 16 placing a second and larger predetermined surface penetrating force on penetrator 13; means 17 sensing with respect to member 11, the differential movement of penetrator 13 in response to the first and second forces; and means, see FIG. 5, translating the differential movement into a hardness indication, e.g. Brinell, Rockwell B and C, Newtons Per Millimeter Squared.

As a feature of the present structure, sensing member 11 is formed as a protective shield surrounding penetrator 13 and is mounted for joint and differential displacement therewith when pressed against surface 12. As here shown, member 11 comprises a sleeve surrounding penetrator 13 and has a distal, surface engaging end 18. Penetrator 13 here comprises an elongated stem 19 having a hardened distal end such as a diamond mounted tip 21 which is normally recessed within the distal end 18 of member 11, the latter being mounted for displacement by surface 12 for engagement of tip 21 with surface 12 and member 11 being mounted and functioning to maintain a reference contact with the surface upon subsequent displacement of the penetrator into the surface in response to the aforementioned first and second forces. Member 11 and penetrator 13 are mounted within a housing 22 having a bottom face 23 engageable with surface 12, member 11 and penetrator 13 being mounted for reciprocation in the housing and normally projecting slightly from face 23, see FIG. 1.

Figure 1:
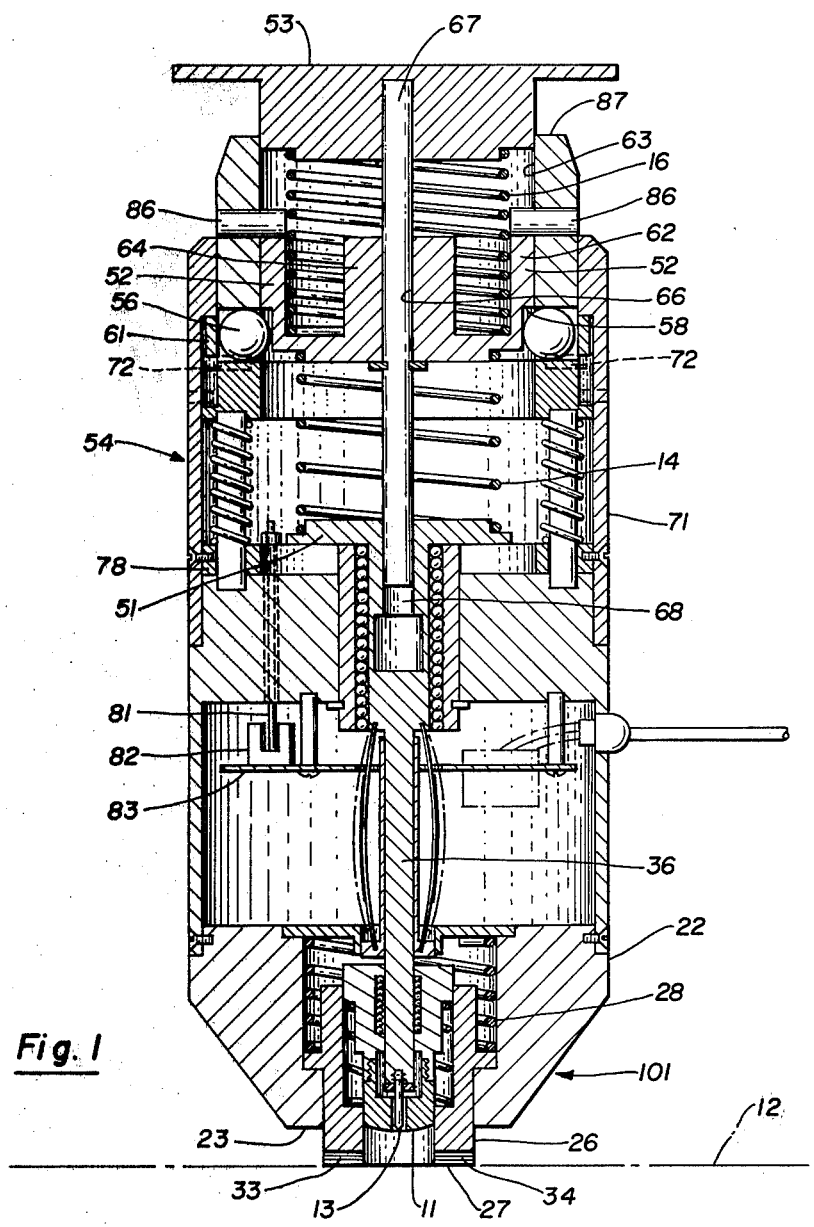
FIG. 1 is a longitudinal cross-sectional view of a material hardness tester constructed in accordance with the present invention.
Figure 2:
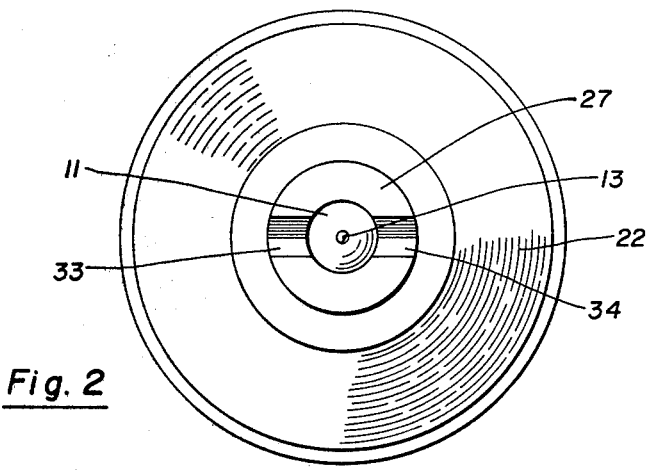
FIG. 2 is a bottom view of the tester.

Preferably, and as shown in the drawing, a second protective sleeve 26 is mounted in housing 22 for reciprocation through and substantially normal to face 23 and in surrounding relation to sleeve 11 and having an end 27 engageable with surface 12, sleeve 26 being movable between a retracted position locating end 27 flush with face 23 for joint engagement with surface 12, see FIGS. 3 and 4, and an extended position projecting normally beyond the distal end 18 of sleeve 11, see FIG. 1. The outer protective sleeve 26 is here biased to its extended position by a helical spring 28 mounted in compression between a shoulder on sleeve 26 and a guide washer 32 secured in housing 22. Distal end 27 of protective sleeve 26 will normally first engage surface 12 as the instrument is applied thereto, see FIG. 1, and preferably the end face 27 of the sleeve is fashioned for engaging and holding the surface for engagement and penetration by penetrator 13. For this purpose, face 27 of member 26 is here formed with diametrically opposed recesses 33 and 34 for locating and holding a curved surface such as round stock for spherical or other curved or non-planar form of surface 12.

Means 17 for sensing the differential movement of the penetrator here comprises a pair of electric strain gauges mounted for sensing relative movement between member 11 and penetrator 13. As will be observed from the drawings, penetrator stem 19 is here mounted to the lower end of a shaft 36 mounted for reciprocation in housing 22 with sleeve 11 having an internally mounted section 37 mounted for reciprocation on shaft 36; and the strain gauges 17 are mounted between shaft 36 and sleeve section 37 to bow in response to differential movement therebetween. As here shown, shaft 36 is formed with a shoulder 38 in longitudinal confronting relation to the internal end 39 of sleeve section 37. A mount 41 is supported on end 39 for rotation about shaft 36, and strain gauges 17, here of elongated bowable form, have their opposite ends supported for endwise displacement on shoulder 38 and mount 41 and will change their bow curvature in response to differential movement between sensing member 11 and shaft 36. As here shown, mount 41 is formed as a shoulder on one end of a reinforcing sleeve 42 surrounding shaft 36 and is mounted within a cylindrical flange 43 formed on washer 32. Shoulder 41 rides on the inner end 39 of the sensing sleeve, the parts being relatively rotatable so that the strain gauges are free of torsional forces which might otherwise be imparted by sleeve 11. At the same time, section 11 is freely movable longitudinally on shaft 36, a lineal bearing 44 being interposed between the parts for this purpose. Sleeve 11 is normally mounted in its retracted position within sleeve 26 by a light helical spring 46 mounted between confronting shoulders 47 and 48 on sleeves 11 and 26.

Various means may be used for applying the predetermined penetrating forces on penetrator 13, as for example, hydraulic or pneumatic actuators or, as in the present showing, spring actuators. The latter have the advantage of simplicity of operating structure with quite precise force characteristics. Accordingly, means 14 here comprises a helical spring mounted for endwise compression between a spring rest 51 on the upper end of shaft 36 and a displaceable spring mount 52, while means 16 comprises a helical spring mounted in longitudinal compression between spring mount 52 and a manually engageable and displaceable handle 53. As a feature of the present invention, handle 53 is used as a means for storing energy in spring 16, and a second manually operable means 54 is provided for transferring energy stored in spring 16 to spring 14 so as to supply the second larger surface penetrating force. As will be observed from FIGS. 1 and 3, springs 14 and 16 are mounted end to end for interacting tandem operation with spring mount 52 mounted between and providing spring rests for confronting ends of the springs. Member 52 is normally anchored against displacement in housing 22 but has its securement controlled by means 54 whereby upon actuation of the latter, member 52 is released for movement relative to the housing permitting transfer of energy between springs 16 and 14. As here shown, this releasable securement is obtained by a plurality of circumferentially spaced balls 56 which are mounted in radial openings 57 in housing 22 and when positioned inwardly toward the center of the housing will be positioned to intercept an annular shoulder 58 on member 52, thus acting as an abutment to stop longitudinal displacement of member 52 within the housing in the direction of the lower end 23 of the housing. Retaining of balls 56 in their inwardly displaced position is here controlled by a ring member 61 normally surrounding balls 56 and preventing their radial outward movement. Member 52 is here formed as a cup-shaped member having a cylindrical side wall 62 mounted for sliding displacement on an internal cylindrical wall 63 of housing 22, and is formed with a central hub 64 having an axial bore 66 for supporting a longitudinal axially extending stem 67 connected to handle 53, the lower end of stem 67 being guided for reciprocation in an axial end bore 68 in spring rest 51 at the internal, upper, end of shaft 36.

In operation, the normally lower end 23 of the tester is applied to surface 12 and handle 53 manually pressed longitudinally of the tester toward surface 12 so as to compress spring 16, see FIGS. 1 and 3, spring mount 52 being held against movement by balls 56. The lower end 27 of protective sleeve 26 first engages surface 12 and as force is applied to handle 53, sleeve 26 will retract bringing the lower end of the surface sensing member 11 into contact with surface 12. Member 11 will then retract to a position flush with lower end 23 of the housing as the latter is brought into contact with surface 12 thus exposing penetrator 13 and causing its point 21 to make an initial penetration into surface 12, the latter action being resisted by spring 14 which applies a first, minor load to the penetrator. This action is accompanied by a small bowing of strain gauges 17 to provide an initial output signal later discussed.

After application of the minor load to penetrator 13, spring mount 52 is released to permit transfer of energy from spring 16 to spring 14 and thus apply the second larger, major, load to the penetrator. This action is here obtained by withdrawing balls 56 from their position intercepting member 52, e.g. by permitting the balls to move outwardly away from the travel of shoulder 58. This action is here accomplished by a sleeve 71 which is mounted in surrounding relation to housing 22 for longitudinal reciprocation and is fitted with internally projecting pins 72 which, on longitudinal displacement of sleeve 71 in the direction of handle 53, will engage and displace ring 61 upwardly from balls 56 thereby permitting their instantaneous outward escape and release spring mount 52 for movement within the barrel of the housing. The transfer of force from spring 16 to spring 14 is, in turn, applied to spring rest 51 at the upper end of shaft 36 thus applying the greater, major, load to the penetrator, at the same time causing further displacement of strain gauges 17. As will be observed, sleeve 71 is formed with an internal recess 73 in which ring member 61 may reciprocate longitudinally of the device, and recess 73 also provides the space into which balls 56 may escape radially to release spring mount 52, when ring member 61 is elevated. Ring 61 operates as a trigger mechanism for releasing balls 56 so that all of the balls are released simultaneously and substantially instantaneously as ring member 61 is moved to clear the widest point of the balls, the pressure on the balls at that instant snapping the ring upwardly away from the balls to permit an instantaneous, simultaneous movement of the balls into recess 73, thus automatically affecting the transfer of force from spring 16 to spring 14 without the intervention or control of the operator. The force transfer is therefore always the same regardless of speed of displacement of sleeve 71.

In the transfer of energy from spring 16 to spring 14, the lower spring is designed to remain open, that is, maintain space between its coils, so as to retain its resiliency whereby the major load is resiliently applied to the penetrator. In other words, at the point of transfer of force from the upper to the lower spring, both springs are in their fully elastic position with neither spring restricted in its longitudinal end-to-end displacement by either any supporting stops or closure of the helical spring loops. When the outer sleeve is lifted to effect the force transfer and to apply the major load to the penetrator, the reaction to the downward thrust of the penetrating point is supported by the static downward force being applied by the operator and the inertia of the mass of the device. In applying the device, the heel of the hands of the user may be conveniently engaged on the upper surface of handle 53 with the fingers of the hands depending to engage sleeve 71. Accordingly, after effecting initial displacement of the tester onto surface 12, bringing the bottom end 23 onto the surface and effecting initial penetration, the operator's fingers will be in position to conveniently engage and elevate sleeve 71 to effect release of balls 56 and the transfer of energy from spring 16 to spring 14. Sleeve 71 is normally biased to a lower position on housing 22, as seen in FIG. 1, by springs 76 here of helical form surrounding guide pins 77 and mounted in compression between housing 22 and a guide ring 78 fastened to the internal periphery of sleeve 71 and having guide openings mounted for reciprocation on pins 77. It is desirable that some means be provided for signaling the application of the major load. This may be accomplished in the electronic circuitry and software hereafter discussed. It may also be accomplished by an optical switch interrupter comprising a shutter 81 here connected to guide ring 78 to depend therefrom into light-interrupting position in a light valve unit 82, here shown mounted on electric circuit board 83. Raising of sleeve 71 will be accompanied by a raising of shutter 81, its removal from its light-interrupting position, and permitting completion of the light circuit and resulting signal output at unit 82.

Displaceable spring mount 52 is here retained within the internal periphery 63 of the housing by pins 86 mounted to the housing side wall and extending internally therefrom to form an abutment for member 52, preventing its withdrawal from the open end 87 of the housing adjacent handle 53. Pins 86 may also form a stop for handle 53 as it is displaced longitudinally into the housing, see FIG. 3. In limiting the upper displacement of member 52, pins 86 also cause initial compression of spring 14 and application of the minor load to penetrator 13 as the instrument is applied to surface 12 of the material being tested.

As hereinabove noted, protective sleeve 26 is here formed with cross grooves 33 and 34 to hold round or spherical (curved) specimens steady and centered for proper penetration by penetrator 13. When measuring the hardness of material having a flat surface 12, both sleeves 26 and 11 will retract to a position flush with end face 23 of the housing. For flat surfaces, the initial minor load force applied to the penetrator will always be the same. However, when the instrument is applied to certain spherical, curved or irregular surfaces, a greater displacement of sensing unit 11 and penetrator 13 may be effected, with a consequent higher minor load penetrating force. It is desirable to sense this greater minor load force so as to locate the ensuing displacement differential on the displacement/hardness scale. This is here accomplished by means sensing a variation from norm of the magnitude of the minor load force and generating an electric signal which may be combined with the electric signal generated by strain gauges 17 by the electronic portion of the device to provide a force compensated hardness indication. As here shown, means 88 comprises an elongated strain gauge having one end 89 mounted as by a pillow block 91 on shoulder 41 which follows the movement of sensing sleeve 11 and its opposite end 92 bearing on a flat wall section 93 of housing 22. Pillow block 91 is here secured to shoulder 41 for joint movement therewith while end 92 of the strain gauge rides upon housing section 93 whereby the strain gauge will be flexed in response to axial displacement of sleeve 11.

Thus, an important feature of the present device, no special surface preparation need ordinarily be made prior to testing. The minor load penetration is designed to pass through rust or other foreign matter on the surface of the material being tested, as well as to penetrate through surface unevenness. A "floating" zero is thus established which is not a given or predetermined zero. It does not matter how deep the penetration is at this point of operation. Upon application of the major load, a further penetration is effected with resulting movement of shaft 36. However, the surface sensing member 11 remains stationary. The resulting differential displacement between these parts is sensed by strain gauges 17. Of importance is the fact that measurements are taken between parts closely associated with the penetrator, thus avoiding measurements taken over large distances and masses which may introduce error due to wear, temperature changes, etc. This is particularly important in a portable instrument where modest penetrating forces are available. Electronic sensing makes possible high accuracy with small penetration measurement very close to the point of penetration. The housing and all associated operating parts may be disregarded and do not effect this measurement. In other words, in the present instrument the critical penetration measurements are made from the surface of the material being tested and the extent of penetration is measured between a closely coupled surface sensing member and the penetrator. Linear bearing 94 provides free relative movement between shaft 36 and housing 22, and lineal bearing 44 provides free relative movement between shaft 36 and measuring sleeve 11. Measurements are taken very close to the point of penetration so that any small tilting of the instrument in making the measurement is not significant. There is no requirement for zeroing the instrument. Preferably, a limit is established to the maximum relative displacement of penetrator shaft 36 and sensing sleeve 11 to limit the maximum stress on strain gauges 17. This is here effected by spacing the lower end 96 of shaft 36 from an internal shoulder 97 on the sensing sleeve 11 to provide abutment limiting maximum differential movement. Maximum inward displacement of sensing sleeve 11 and penetrator 13 under abnormal minor load conditions described above is effected by engagement of upper end 39 of the sleeve with flange 43 on guide washer 32.

The portable hardness tester disclosed herein offers exceptional versatility and accuracy through the use of a programable microcomputer to control the operation of the instrument and to perform calculations. The electronic circuitry of the tester is seen in FIG. 5 to comprise five basic functional units: the tester head 101; the head interface unit 102; the processor unit 103; the user interface unit 104; and user input-output devices 105.

The tester head 101 is the unit which the user places against the surface 12 of the material which is to be penetrated. The electrical components of the tester head include: a penetrator position transducer 106; a force transducer 107; a temperature transducer 108; and a major load/minor load switch 109.

The penetrator position transducer 106 senses the differential movement of the penetrator 13 in response to the first (minor load) and second (major load) forces and generates an electrical signal in response thereto. In the preferred embodiment, the penetrator position transducer 106 employs a pair of strain gauges 17 mounted for sensing relative movement between member 11 and penetrator 13. The strain gauges, which are connected in a full bridge configuration, are supplied with a precision d.c. reference voltage. As the strain gauges bow in response to the movement of the penetrator, their resistance changes, thus providing a variable d.c. output voltage. After application of the minor load to the penetrator, the processor unit 103 reads the output signal from the strain gauges. The processor reads the output signal again after the application of the major load. The difference between the two readings is converted by the processor into an indication of the hardness of the material which has been penetrated. This conversion process will be more fully explained in the portion of the instant specification dealing specifically with the system's program which controls the processor.

The force transducer 107 senses the magnitude of the force applied to the penetrator and generates an electrical signal in response thereto. In the preferred embodiment the force transducer employs strain gauge 88 supplied with a precision d.c. reference voltage. This strain gauge senses movement of the sensing sleeve 11 relative to the tester head housing 22. The relative movement of the two aforementioned mechanical components is proportional to the force which is applied to the penetrator. As the force transducer strain gauge 88 is deformed in response to the applied penetrator force, its resistance changes thus providing a variable d.c. output voltage. The processor 103, under program control, compares the output of this force transducer strain gauge to a predetermined value residing in memory. If the strain gauge output varies significantly from the predetermined value, the processor adjusts the hardness indication to compensate for variations in the applied force. The output from the force transducer 107 is used by the processor 103 to provide force compensated hardness indications.

The temperature transducer 108 senses the ambient operating temperature of the tester head 101. In the preferred embodiment, the temperature transducer is an integrated circuit temperature sensor chip which provides a linear d.c. output voltage as a function of head temperature. A thermistor, base-emitter semiconductor junction, or other well known means of producing a variable d.c. voltage in response to temperature may also be used. The output of the temperature transducer 108 is read by the processor 103 which makes an appropriate adjustment in the hardness indication to compensate for the effects of temperature on the electrical and mechanical components of the tester head 101.

The major load/minor load switch 109 changes state upon initiation of the major load force. In the preferred embodiment, this switch is an opto interrupter 82 whose light path is mechanically blocked by shutter 81 until the major load is applied. The output of the major load/minor load switch is supplied to the processor 103 and is used to indicate to the processor that the major load has been applied. The processor, upon sensing a change of state in switch 109, reads the output of the penetrator position transducer 106 to determine major load penetrator displacement. Switch 109 can be completely eliminated if the processor 103 is programmed to recognize the application of the major load through recognizing a significant change in the output of the penetrator position transducer 106 as the major load is applied.

The head interface unit 102 functions to translate, condition, and convert the outputs from the tester head into digital signals which can be read by the processor 103. In the preferred embodiment, the head interface unit is physically located within the tester head 101 on circuit board 83 in order to minimize noise pickup which might occur during the transmission of the tester head output signals to a remotely mounted head interface unit.

The head interface unit 102, in the preferred embodiment, employs an analog multiplexer 112. The variable d.c. outputs from the penetrator position transducer 106, force transducer 107, and temperature transducer 108 are connected to the input of analog multiplexer 112. The output of the analog multiplexer 112 is a single line which is connected to the input of filter amplifier circuit 114. Processor 103 controls which of the inputs to analog multiplexer 112 appears at the output by means of select line 113. The analog multiplexer 112 allows the use of a single filter amplifier circuit 114 and a single analog to digital converter circuit 115 to process the outputs from transducers 106, 107 and 108 resulting in a significant savings in parts and costs.

Filter amplifier circuit 114 contains filters and amplifiers which reduce noise and condition the analog signals which appear at its input so that the output is a low noise d.c. signal suitable for input to the analog to digital converter circuitry 115 which follows. Filter amplifier circuit 114 employs standard instrumentation amplifiers, low pass filters, and associated compensation and conditioning circuitry.

Analog to digital converter circuit 115 converts the d.c. analog voltage which appears at its input to a digital output which is read by processor unit 103. In the preferred embodiment, circuit 115 is actually an analog to frequency converter which is essentially a voltage controlled oscillator. The output pulses are counted during a standard time interval by processor unit 103 and used to give a digital value which corresponds to the magnitude of the analog signal which appears at the input of circuit 115. The head interface unit 102 also contains schmidt trigger and level translator circuit 116 which converts the output from major load/minor load switch 109 into a logic signal which is compatible with processor unit 103. In alternative embodiments which use software to recognize the application of the major load force, circuit 116 and switch 109 can be eliminated.

Processor unit 103 performs the major control functions and all arithmetic calculations associated with the operation of the hardness tester. Processor unit 103 contains a central processor unit (CPU) 118, a read only memory (ROM) 119, and a random access memory (RAM) 120. Processor unit 103 also contains input-output, timing, and interface circuitry normally associated with digital microprocessors. The overall system's program is stored in ROM 119. RAM 120 provides temporary storage and buffering of data. CPU 118 is, in the preferred embodiment, a standard 8 bit microprocessor chip which is controlled by the program residing in ROM 119. CPU 118 performs all of the mathematical calculations and data manipulations necessary to convert the digitized outputs from the tester head 101 into accurate hardness readings which are displayed in digital form. Processor 103 also accepts user inputs which command the processor to supply hardness readings in various standard scales (Brinell, Rockwell, Newtons Per Millimeter Squared), to perform various statistical calculations such as average hardness, and to tag hardness readings with user inputed information such as the date, sample number, etc. Processor unit 103 communicates with the various other functional components of the hardness tester via system bus 121.

User input-output devices 105 allow the user to control the operation of the hardness tester and provide the user with outputs by means of digital display 123, hard copy printer 124, and beeper 125. User input information is fed to processor 103 by means of keyboard 126 and scale select switch 127. Keyboard 126 allows a user to input such information as the date, sample number, and other alphanumeric information associated with a particular reading or series of hardness readings. By depressing the appropriate function button, the user may command the processor unit 103 to perform various statistical calculations and to display and/or print either individual hardness readings or an averaged reading. Scale select switch 127 is used to select the particular scale (Brinell, Rockwell B or C, or Newtons Per Millimeter Squared) in which the hardness indication is to be displayed. The processor 103, under program control, reads the setting of the scale select switch 127 and converts the hardness data into the proper scale. Beeper 125 is used as an operator prompting device to indicate such events as aberrant readings, the readiness of the tester to perform additional penetrations, and as an indication of various system faults. Digital display 123 provides temporary display of hardness readings and other relevant digital information. Printer 124 provides hard copy records of hardness data and can print time, date, and other alphanumeric information.

User interface unit 104 contains output device interface 129 and input device interface 130. The function of user interface unit 104 is to interface the various user input and output devices 105 with processor 103. Input device interface 130 contains the circuitry necessary to convert the inputs from keyboard 126 and scale select switch 127 into digital signals compatible with processor unit 103. Output device interface 129 contains circuitry which allows output devices 123, 124, and 125 to be driven by digital signals from processor unit 103. Output device interface 129 contains the usual driver, decoder, and level translating circuits associated with the operation of digital displays, printers, and audible indicators. Input device interface 130 contains circuitry which debounces, and otherwise conditions the signals supplied by user input devices 126 and 127.

Figure 6:
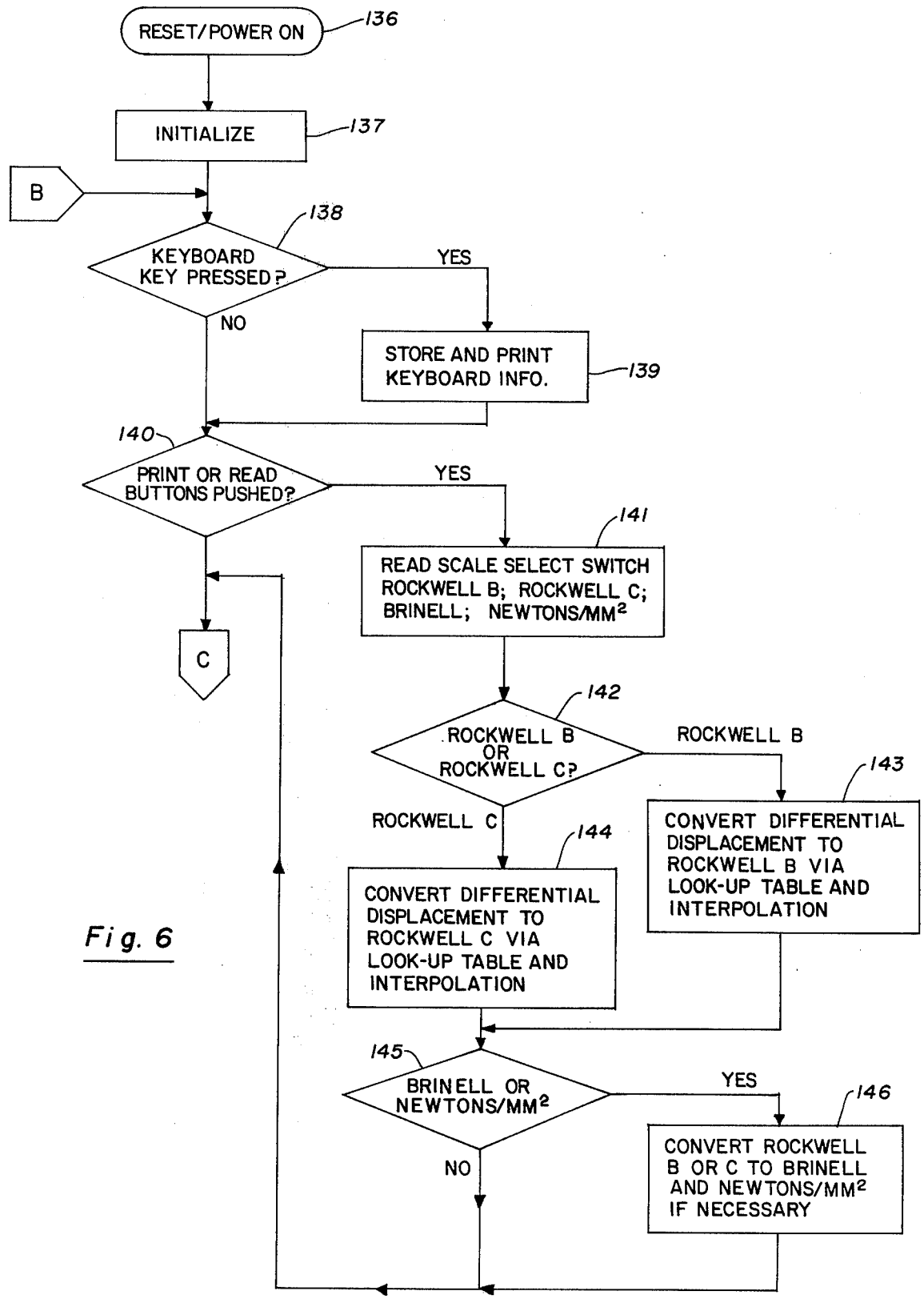
FIGS. 6, 7 and 8 are flow diagrams of the system's program of the present invention.

The overall operation of the instant hardness tester can be best understood by joint examination of the previously described hardware and the system's program which controls the operation of CPU 118. The overall system's program resides in ROM 119 and is illustrated, in simplified flow chart form, in FIG. 6 and FIG. 7. FIG. 8 details, in flow chart form, a particular portion of the overall program which performs conversion of the head output data into compensated hardness readings. Although the flow charts are, for the most part, self explanatory, the individual program steps have been numbered to aid in discussing their function and operation.

Upon sensing either a reset or a power-up condition program step 136 proceeds to step 137 which initializes the system thus making it ready to perform readings, calculations, and other program functions. Once initialization is complete, program step 138 looks to see if a key on keyboard 126 has been pressed by the user. If a pressed key is sensed the program proceeds to step 139 which stores and prints the alphanumeric information inputted by the user via keyboard 126. If program step 138 does not sense a pressed key, it proceeds to step 140 which looks to see if the user has pressed either the print or read special function buttons. If the print or read button has been pushed, the program proceeds to step 141 which reads the output from the scale select switch 127.

Scale select switch 127 selects, under user control, the scale in which the hardness reading is to be presented, i.e. Rockwell B, Rockwell C, Brinell, or Newtons Per Millimeter Squared. Step 142 follows 141 and asks whether Rockwell B or Rockwell C scales have been selected. If Rockwell B has been selected, the program proceeds to step 143 which converts the differential displacement sensed by penetrator position transducer 106 into a Rockwell B hardness indication by means of a look-up table which resides in ROM 119. This look-up table is derived originally by penetrating samples of known Rockwell B hardness and correlating the resultant output from penetration position transducer 106 to the known Rockwell B reading. Interpolation is used to determine the equivalent Rockwell B hardnesses which lie between two known values in the look-up table. Step 144 follows step 142 when the user selects the Rockwell C scale. Step 144 is completely analogous to step 143 except for the fact that the differential displacement readings from the penetration position transducer 106 are converted to Rockwell C readings. Step 145 asks whether either the Brinell or Newtons Per Millimeter Squared scale has been selected and if so proceeds to step 146 which converts Rockwell B or C hardness readings to Brinell and Newtons Per Millimeter Squared as required. Step 146 performs the conversion by means of a look-up table which resides in ROM 119.

Figure 7:
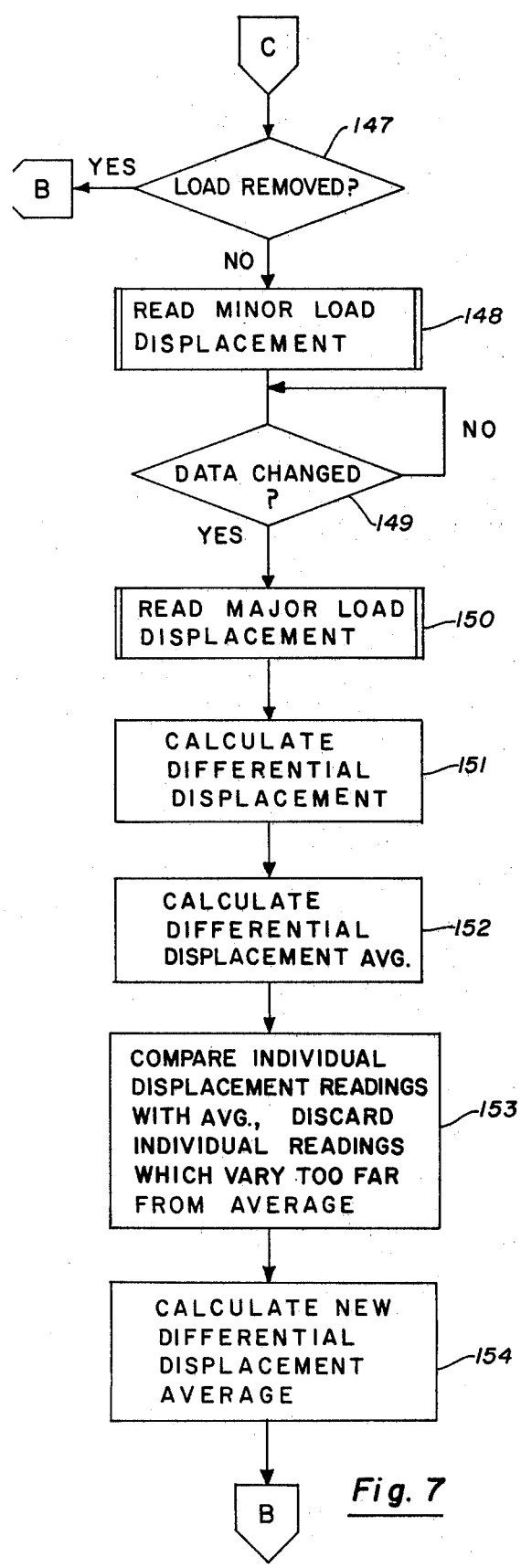
Figure 8:
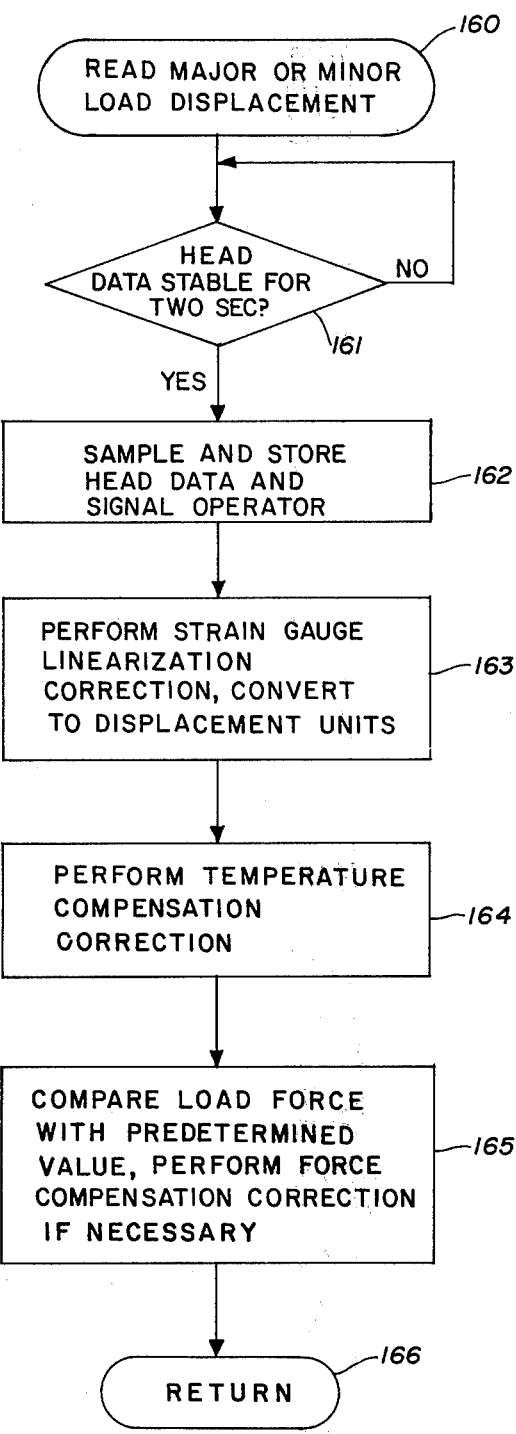

Proceeding now to FIG. 7, step 147 looks to see whether the load has been removed which would indicate the completion of a test. If the load has been removed, the program returns to step 138 and proceeds from that point. If the load has not been removed, the program proceeds to step 148 which reads the minor load displacement. Step 149 asks whether there has been a change in the data output from penetrator position 106 which would indicate initiation of the major load. In the embodiment of the device illustrated in FIG. 5, step 149 reads the data from switch 109, rather than the data from transducer 106 to determine whether the major load has been applied. If step 149 senses that the major load has been applied, the programs proceed to step 150 which reads the major load displacement from penetrator position transducer 106. The next program step, 151, calculates the differential displacement i.e., the difference in the penetrator position transducer output produced by the minor load and major load. Program step 152 calculates the average differential displacement by averaging a plurality of individual readings. Step 153 compares individual displacement readings with the average calculated in step 152 and discards individual readings which vary too far from the average. Program step 154 calculates a new corrected differential displacement average by averaging the readings not discarded in program step 153. After step 154 the program returns to step 138.

The program detailed in FIG. 8 can be viewed as a subroutine which is called into play when either step 148 or 150 is reached. Upon sensing the program command to read either the major or minor load displacement, step 160 proceeds to step 161 which looks to see if the data output from head 101 has been stable for approximately two seconds. If the data has not yet settled, step 161 loops until a stable data output is read. Once the data has stabilized, the program proceeds to step 162 which samples and stores the head data from the various transducers then signals the operator via beeper 125 to indicate that the data has been read and stored. Program step 163 performs the strain gauge linearization correction via an experimentally derived look-up table residing in ROM 119 and converts the output of penetration position transducer strain gauges into displacement units. Program step 164 performs temperature compensation corrections, if necessary, by means of a look-up table experimentally derived and residing in ROM 119. Program step 165 compares the output from force transducer 107 to a predetermined value in order to determine whether force compensation corrections are necessary. If the output of force transducer 107 varies significantly from the predetermined value, step 165 preforms a force compensation correction by means of an experimentally derived look-up table which resides in ROM 119. Step 166 returns from the subroutine to the general system's program following either step 148 or 150.

The use of experimentally derived look-up tables in performing the various units conversions and compensations for temperature and force allows great accuracy and flexibility. Interpolation is used to calculate points which lie between the discrete values in the look-up tables. This reduces the amount of memory space required. In the alternative, compensation and units conversion formulas may be used in place of look-up tables.

What is claimed is:

1. A portable material hardness tester comprising:
a surface sensing member yieldably mounted for engagement with the surface of material to be tested;
a penetrator yieldably mounted adjacent said member for joint contact with said surface;
said member being positioned as a protective shield for said penetrator and being mounted for joint and differential displacement therewith when pressed against said surface;
said member including a sleeve surrounding said penetrator and having a distal, surface-engaging, end;
said penetrator having a surface-engaging tip;
means for placing a first predetermined surface penetrating force on said penetrator;
means placing a second and larger predetermined surface penetrating force on said penetrator;
means sensing with respect to said member the differential movement of said penetrator in response to said first and second forces;
said member being mounted for displacement by said surface for engagement of said tip with said surface, and said member being mounted to maintain a reference contact with said surface upon subsequent displacements of said penetrator into said surface in response to said first and second forces;
a housing having a face engageable with said surface, with said member and penetrator being mounted for reciprocation in said housing and normally projecting from said face; and
means translating said differential movement into a hardness indication.

2. The device of claim 1, and
a second protective sleeve mounted in said housing for reciprocation through and substantially normal to said face and in surrounding relation to said first-named sleeve and having an end engageable with said surface, said second sleeve being movable between a retracted position locating said end thereof at said face for joint engagement with said surface and an extended position projecting normally beyond said first-named sleeve end; and
means biasing said second sleeve to its extended position.

3. The device of claim 2, said second sleeve end being formed with diametrically opposed recesses for locating and holding a curved surface for engagement by said penetrator.

4. The device of claim 1,
a shaft mounted for reciprocation in said housing and mounting said penetrator at an end thereof;
said sleeve being mounted for reciprocation on said shaft; and
an electric strain gauge mounted between said shaft and sleeve to bow in response to differential movement therebetween.

5. The device of claim 4, said shaft providing a shoulder in confronting relation to the internal end of said sleeve opposite said distal, surface engaging end thereof;
a mount supported on said internal end for rotation about said shaft;
a pair of elongated bowable strain gauges having their opposite ends supported for endwise displacement on said shoulder and mount and changing in bow curvature in response to differential movement between said sleeve and shaft.

6. The device of claim 1,
said first-named means comprising a first spring mounted to provide the aforementioned yieldable mount for said penetrator;
said second-named means comprising a second spring and first manually operable means for storing energy therein; and
second manually operable means for transferring energy stored in said second spring to said first spring.

7. The device of claim 6,
said differential movement sensing means generating a first electric signal as a function of a first penetration by said first force and a second electric signal as a function of a second penetration by said second force; and
means providing an operator signal upon completion of generation of said first signal.

8. The device of claim 1,
said first-named means comprising a first spring mounted to and between said shaft and housing to provide the aforementioned yieldable mount for said penetrator;
said second-named means comprising a second spring and manually operable means for storing energy therein; and
second manually operable means for transferring energy stored in said second spring to said first spring.

9. The device of claim 8,
said sensing means comprising a pair of elongated bowable strain gauges having their opposite ends supported for endwise displacement on said shaft and sleeve and changing in bow curvature in response to differential movement between said sleeve and shaft.

10. The device of claim 8,
said springs being of helical form and mounted end-to-end for interacting tandem operation;
a second member mounted between and providing spring rests for confronting ends of said springs; and
means releasably securing said second member to said housing and being formed and connected to said second manually operable means for actuation thereby to release said second member for movement relative to said housing permitting transfer of energy between said springs.

11. The device of claim 10,
said second-named means comprising a handle mounted for reciprocation on said housing coaxially of said springs and connected to the end of said second spring opposite to said confronting ends, and functioning on manual displacement relative to said housing to compress said second spring on said second member.

12. The device of claim 10,
said last-named means comprising a plurality of circumferentially spaced balls carried by said housing in surrounding relation to and in position locking the movement of said second member; and
said second manually operable means being formed and functioning to simultaneously release said balls for movement away from their interlocking position with said second member.

13. The device of claim 12,
a free-floating ring surrounding and retaining said balls in locking position;
a second sleeve mounted at the outside of said housing for manual engagement and reciprocation relative to said housing and being formed with an enlarged annular chamber for receiving said balls; and
said sleeve being connected to said ring and being movable to a position simultaneously displacing said ring to release said balls and to register said chamber and balls.

14. The device of claim 10,
said differential movement sensing means generating a first electric signal as a function of a first penetration by said first force and a second electric signal as a function of a second penetration by said second force;
said translating means comprising an electric circuit and readout for converting said signals into a hardness indication at said readout; and
an electric switch connected for actuation by said last-named means upon release of said second members and connected to said circuit enabling the operation thereof by said second signal.

15. A material hardness tester comprising:
a surface sensing member yieldably mounted for engagement with the surface of material to be tested;
a penetrator movably mounted adjacent said member for engagement with said surface for joint contact with said surface;
a first spring connected to said penetrator and providing a first predetermined surface penetrating force thereon;
a second spring and means storing energy therein connected to place a second and larger predetermined surface penetrating force on said penetrator;
means sensing with respect to said member the differential movement of said penetrator in response to said first and second forces and generating a first electric signal as a function of said differential movement;
means sensing a variation from norm of the magnitude of said first force and generating a second electric signal; and
means translating said first and second electric signals into a force compensated hardness indication.

16. The device of claim 15,
said second- and third-named means comprising electric strain gauges.

17. The device of claim 16,
said member comprising a sleeve surrounding said penetrator and having a distal, surface engaging end;
said penetrator having a surface engaging tip normally recessed within said member end;
said member being mounted for displacement by said surface for engagement of said tip with said surface, and said member being mounted to maintain a reference contact with said surface upon subsequent displacement of said penetrator into said surface in response to said first and second forces;
a housing having a face engageable with said surface, said member and penetrator being mounted for reciprocation in said housing and normally projecting from said face;
a shaft mounted for reciprocation in said housing and supporting said penetrator at an end thereof;
said sleeve being mounted for reciprocation on said shaft;
one of said strain gauges being mounted between said shaft and sleeve to bow in response to differential movement therebetween; and
the other of said strain gauges being mounted between said sleeve and housing and sensing the relative positions thereof.

* * * * *